(12) United States Patent
de Menezes

(10) Patent No.: US 8,360,989 B2
(45) Date of Patent: Jan. 29, 2013

(54) VALSALVA LUNG PRESSURE MONITORING SYSTEM AND METHOD

(75) Inventor: Alexandre Carvalho de Menezes, Belo Horizonte (BR)

(73) Assignee: Laborie Medical Technologies Canada ULC, Mississauga, Ontario (CA)

( * ) Notice: Subject to any disclaimer, the term of this patent is extended or adjusted under 35 U.S.C. 154(b) by 257 days.

(21) Appl. No.: 12/723,634

(22) Filed: Mar. 13, 2010

(65) Prior Publication Data

US 2010/0234758 A1 Sep. 16, 2010

Related U.S. Application Data

(60) Provisional application No. 61/159,975, filed on Mar. 13, 2009.

(51) Int. Cl.
*A61B 5/00* (2006.01)
*A61B 5/03* (2006.01)

(52) U.S. Cl. ..................... 600/561; 600/301
(58) Field of Classification Search ................. 600/301, 600/561
See application file for complete search history.

(56) References Cited

U.S. PATENT DOCUMENTS

| | | | |
|---|---|---|---|
| 6,120,442 A * | 9/2000 | Hickey | 600/300 |
| 2004/0106874 A1 | 6/2004 | Eigler et al. | |
| 2005/0038328 A1 | 2/2005 | Stoehrer et al. | |
| 2005/0288603 A1 * | 12/2005 | Goping | 600/561 |
| 2006/0207611 A1 * | 9/2006 | Anonsen | 128/859 |
| 2007/0255090 A1 | 11/2007 | Addington et al. | |
| 2010/0137736 A1 * | 6/2010 | Addington et al. | 600/546 |
| 2010/0137737 A1 * | 6/2010 | Addington et al. | 600/546 |

OTHER PUBLICATIONS

Nitti et al, "Correlation of Valsalva Leak Point Pressure with Subjective Degree of Stress Urinary Incontinence in Women", Journal of Urology, Lippincott Williams & Wilkins, Baltimore, MD, US LNKD-DOI:10.1016/ S0022-5347(01)66619-9, vol. 155, No. 1, Jan. 1, 1996, pp. 281-285, XP005576782 ISSN: 0022-5347.*

* cited by examiner

*Primary Examiner* — Sean Dougherty
(74) *Attorney, Agent, or Firm* — Cahn & Samuels, LLP

(57) ABSTRACT

A system and method in at least one embodiment includes a pressure monitor, mouthpiece and tubing connecting the pressure monitor and mouthpiece that measures coughed air to monitor Valsalva lung pressure in order to measure the abdominal pressure surrounding the bladder. The system and method provides a non-invasive and convenient system and method for determining an abdominal Leak Point Pressure that utilizes a mouthpiece connected to a pressure monitor in order to measure the lung pressure of an individual such that the abdominal pressure surrounding the bladder is determined.

19 Claims, 4 Drawing Sheets

VALSALVA LUNG PRESSURE MONITORING SYSTEM AND METHOD

This patent application claims the benefit of U.S. Provisional Patent Application No. 61/159,975, filed Mar. 13, 2009, which is hereby incorporated by reference.

I. FIELD OF THE INVENTION

This invention relates to a system and method for monitoring Valsalva lung pressure in order to determine the abdominal pressure surrounding the bladder. More particularly, this invention relates to a non-invasive and convenient system and method for monitoring abdominal pressure that in at least one embodiment utilizes a mouthpiece connected to a pressure monitor to measure the lung pressure of an individual such that the abdominal pressure surrounding the bladder is determined.

II. BACKGROUND OF THE INVENTION

Several organs, muscles and nerves, e.g., kidneys, ureter, bladder, urethra, sphincters, and various other tissue, interact to collect, store and release urine. In vertebrates two kidneys filter waste and excess water from the bloodstream to form urine. The urine then flows from the kidneys to the bladder via a hollow muscular tube called a ureter. Normal urine flow occurs in only one direction, i.e., from the kidneys to the bladder. When urine backs up or flows in the other direction, i.e., from the bladder to the kidneys, infection or damage to the kidneys can occur.

The bladder is a hollow, balloon-shaped organ that sits in the pelvis. The bladder stores urine until the body is ready to release it. Normal adult human bladders can comfortably hold about 16 ounces or 2 cups of urine before needing to empty. Urine is produced and therefore the bladder fills based on the amount of excess water the body attempts to rid itself of. The bladder connects to another hollow tube, called the urethra, which allows the urine to pass outside the body. Circular muscles or sphincters surround and close tightly around the base of the bladder and urethra to prevent urine from leaking. Nerves in the bladder send a signal to the brain to let the body know when its time to urinate and the sphincters are relaxed to allow urine to pass.

The involuntary leakage of urine from the bladder is called urinary incontinence or stress incontinence. Stress incontinence is the loss of small amounts of urine associated with coughing, laughing, sneezing or other physical activities. This condition is essentially due to weak pelvic floor muscles. Stress incontinence is often caused by physical changes, such as pregnancy, childbirth, and menopause in women, and following a prostatectomy in men. While stress incontinence is the most common form of incontinence, it is treatable.

The field of urodynamics is devoted to studying and testing the functional disorders of the lower urinary tract which is comprised of the bladder and urethra. Urodynamics seeks to objectively confirm the existence of urological pathologies, such as urinary incontinence and blocked urine flow. In the field of urodynamics, the abdominal (Valsalva and coughing) Leak Point Pressure (LPP) of the human bladder is measured. Abdominal LPP is a very important measurement used to quantify the degree of incontinence in order to direct the right treatment. Measuring the abdominal LPP of the human bladder has traditionally required invasive, complicated, inconvenient and/or unclean procedures. These procedures typically include the insertion of a measuring device inside the pelvic area of the body, e.g., inserting a balloon catheter into the bladder or rectum. The undesirable nature of these procedures often acts as a deterrent to testing for many individuals in need of testing.

III. SUMMARY OF THE INVENTION

This invention in at least one embodiment provides an apparatus for measuring an abdominal pressure, including a pressure monitor, wherein the pressure monitor includes a pressure chamber; a transducer in fluid communication with the pressure chamber, wherein the transducer generates a pressure signal; and a controller in communication with the transducer, wherein the controller outputs a pressure reading based on the pressure signal where the pressure reading reflects abdominal pressures; tubing connected to the pressure monitor to establish a pathway for air to travel from the tubing to the pressure chamber; an airway filter connected to the tubing; and a mouthpiece connect to an opposite end of the tubing from the pressure monitor.

This invention in at least another embodiment provides a method for measuring an abdominal leak point pressure with a device having a pressure monitor and tubing connecting a mouthpiece to the pressure monitor, including placing the mouthpiece in the mouth of a patient; having the patient perform Valsalva maneuvers such that air is expelled from the lungs and forced through the tubing; measuring a pressure of the expelled air with the pressure monitor; and checking the patient for a urinary leak.

This invention in at least another embodiment provides a method for measuring an abdominal leak point pressure with a device having a pressure monitor including a sensor and tubing connecting a mouthpiece to the pressure monitor, including placing the mouthpiece in the mouth of a patient, wherein the mouthpiece includes a lip flange and bite wings in order to form a seal in the mouth; having the patient perform a Valsalva maneuver such that air is expelled from the lungs and forced through the tubing; measuring a pressure of the expelled air with the pressure monitor; receiving a signal to mark the pressure reading for an event; storing the measured pressure in a memory and annotating the measured pressure data when the signal to mark is received; and providing the measured pressure as representative of abdominal pressure.

IV. BRIEF DESCRIPTION OF THE DRAWINGS

The present invention is described with reference to the accompanying drawing, wherein.

Given the following enabling description of the drawings, the system and method should become evident to a person of ordinary skill in the art.

V. DETAILED DESCRIPTION OF THE DRAWINGS

The present invention in at least one embodiment includes a system and method that monitors Valsalva lung pressure to determine the abdominal Leak Point Pressure (LPP) of the bladder. The present invention in at least one embodiment provide a non-invasive and convenient system and method that utilizes a mouthpiece connected to a pressure monitor via tubing to provide a lung pressure measurement that is used to determine the LPP of the bladder. In at least one embodiment the present invention includes a button or other interface for determining and storing data such as the peak value of the Valsalva lung pressure.

The system and method of the present invention utilize a novel correlation between a patient's lung pressure (Plung) and abdominal pressure (Pabd), i.e., Valsalva Leak Point Pressure (LPP). Research has revealed the existence of a close correlation between a patient's breathed lung pressure (Plung) and abdominal pressure (Pabd), i.e., abdominal pressure is typically within plus or minus ten percent (+/−10%) of measured lung pressure. This correlation allows a patient's lung pressure to be measured non-invasively by expelling air into a pressure measuring device and then utilizing the lung-abdominal pressure correlation to translate the measured lung pressure into an abdominal Leak Point Pressure (LPP). In at least one embodiment of the present invention, the pressure correlation is not sensitive to a patient's age, gender, body mass index (BMI), or other similar measures that tend to impact lung pressure.

Figure 1:
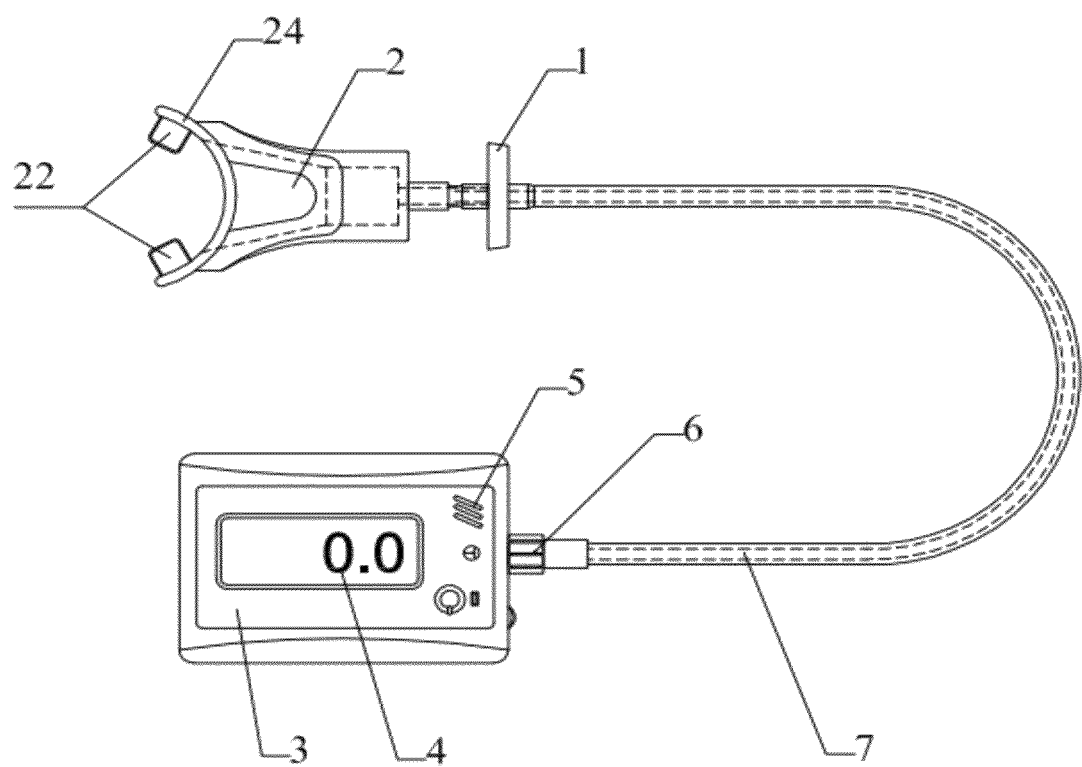
FIG. 1 illustrates a leak point pressure measuring device according to an embodiment of the present invention.

FIG. 1 illustrates an exemplary embodiment of the abdominal leak point pressure system of the present invention. The abdominal Leak Point Pressure (LPP) system includes an airway filter 1, a mouthpiece 2, a pressure monitor 3, a display 4 and tubing 7. The abdominal LPP system measures LPP by monitoring the pressure produced by the expelled air of a patient during a series of coughs or Valsalva maneuvers. Pressure monitor 3 includes a sensor that measures the expelled air pressure. Pressure monitor 3 is connected to one end of tubing 7. Mouthpiece 2 is connected to an opposite end of tubing 7 from pressure monitor 3, and these three components together form a pressure chamber. Mouthpiece 2 is preferably designed to fit in the mouth of the patient so that the pressure of the expelled air is not lost and is accurately measured by pressure monitor 3. Pressure monitor 3 includes a pressure measuring transducer that produces an electrical signal representative of the pressure against the transducer. The electrical signal in most embodiments is converted by a processor into the measured pressure reading to be sent to display. Pressure monitor 3 is preferably connected to tubing 7 via a substantially leak proof fitting 6, for example, a Luer-lock connector.

In use, a patient inserts the mouthpiece 2 into the mouth, bites down on the bite tabs 22 and places his/her lips over and around the flange 24. Once the mouthpiece is securely in the mouth of the patient, the patient performs several Valsalva maneuvers, e.g., coughing five (5) times. The coughs expel air from the lungs of the patient and through tubing 7 to pressure monitor 3. Pressure monitor 3 measures the pressure of the expelled air traveling through tubing 7 and outputs a signal to display 4. Pressure monitor 3 may also include wired or wireless communication module, e.g., Bluetooth, to allow measured data to be transferred to and/or received from external devices or to alert, for example, a testing laboratory or medical personnel.

In an alternative embodiment, the abdominal leak point pressure measuring system may also include a digital display 4 and/or an audible speaker 5 in order to provide different types and levels of alerts. Digital display 4 is capable of providing pressure measurements in a variety of units. Digital display 4 may also provide a visual indication of a leak, e.g., "L" or flash. Digital display 4 in at least one embodiment also provides the most recent high measured pressure as a second display measured pressure. The abdominal leak point pressure measuring system may also include a speaker 5 for providing audible alerts.

In other alternative embodiments, the abdominal leak point pressure measuring system may include tubing 7 of various lengths including no tubing. When no tubing is present, the mouthpiece 2 is connected to and/or integrally formed with the pressure monitor 3.

In one alternative embodiment, the abdominal leak point pressure measuring system includes an airway filter 1 mounted in tubing 7 between mouthpiece 2 and pressure monitor 3. Airway filter 1 is disposed along tubing 7 to protect pressure monitor 3 by preventing any solid matter or debris from coming into contact with the pressure monitor 3. Alternatively, the airway filter 1 may be located in the mouthpiece 2.

In another alternative embodiment, the abdominal leak point pressure measuring system includes a mouthpiece 2 connected directly to pressure monitor 3. In another alternative embodiment, the abdominal leak point pressure measuring system includes tubing 7 and pressure monitor 3.

Figure 2:
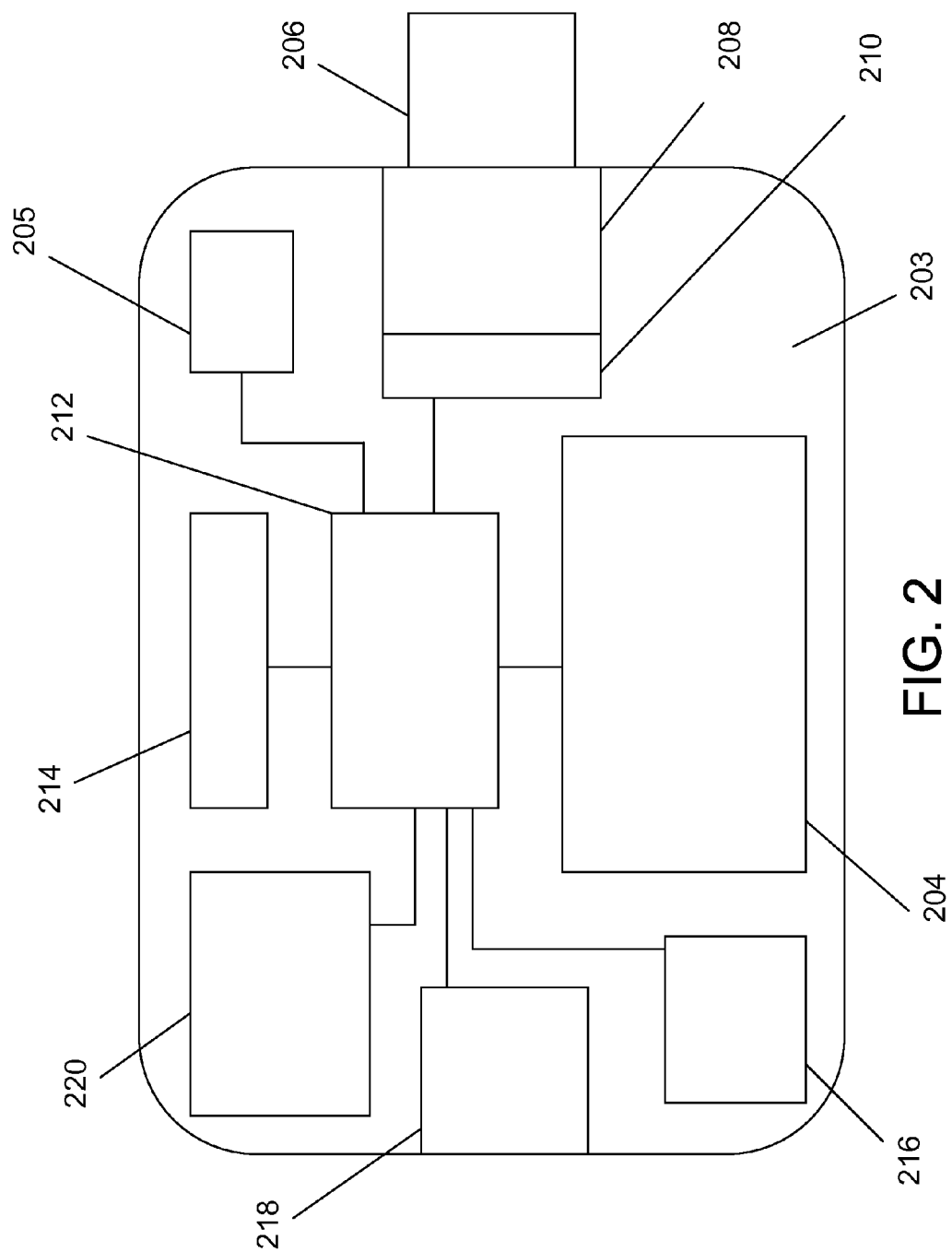
FIG. 2 illustrates a schematic diagram of the leak point pressure measuring device according to an embodiment of the present invention.
Figure 3A:
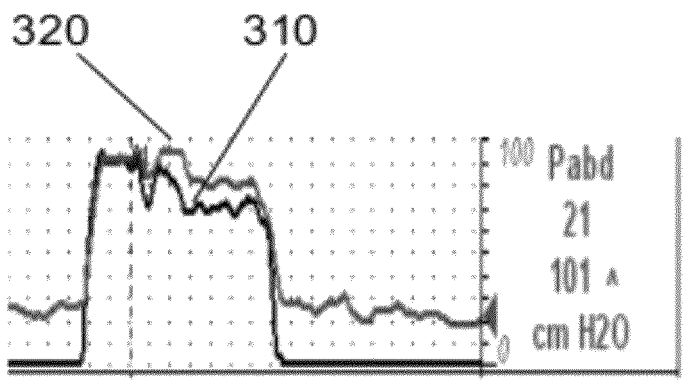
FIGS. 3A-3D illustrate graphs of the experimental measurements of a patient's lung pressure (Plung) and abdominal pressure (Pabd) during Valsalva maneuvers.
Figure 3B:
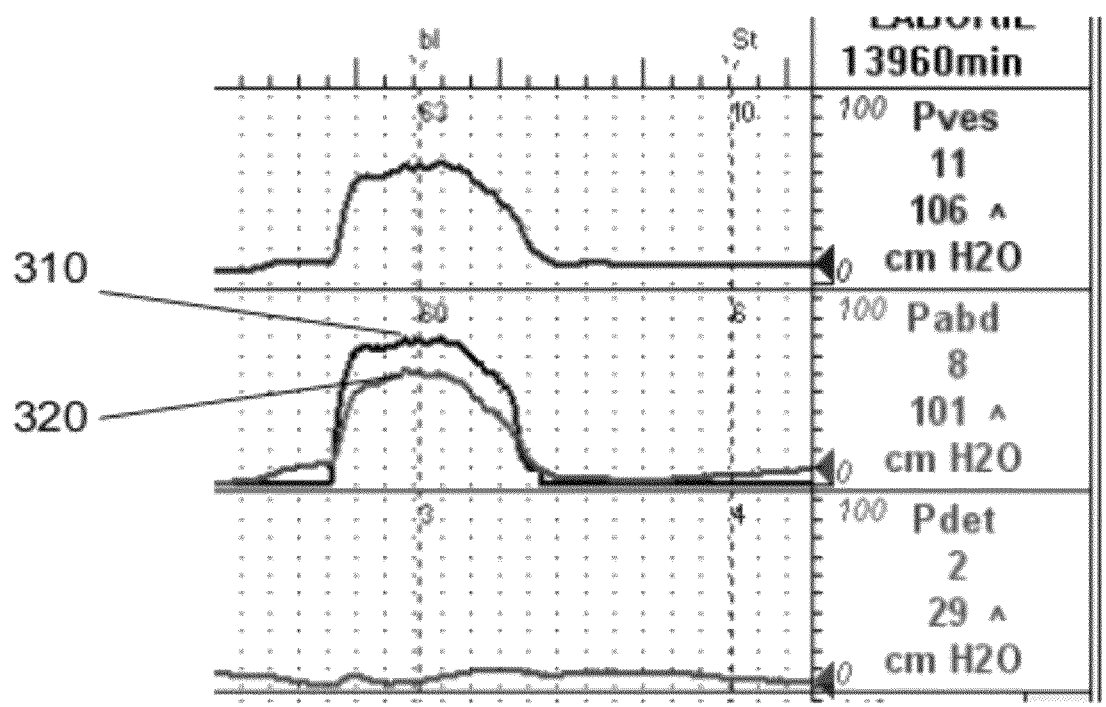
Figure 3C:
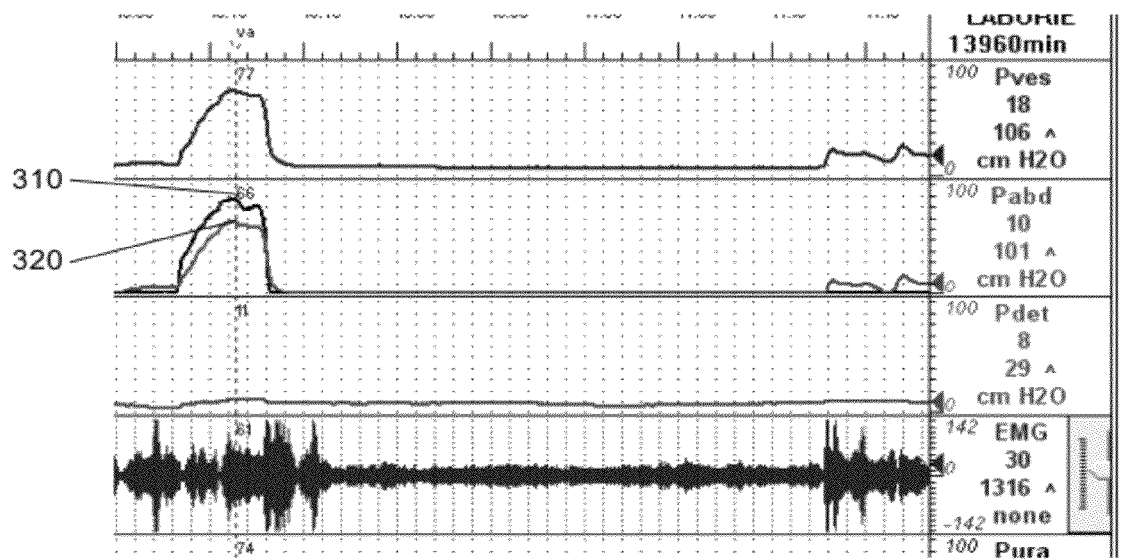
Figure 3D:
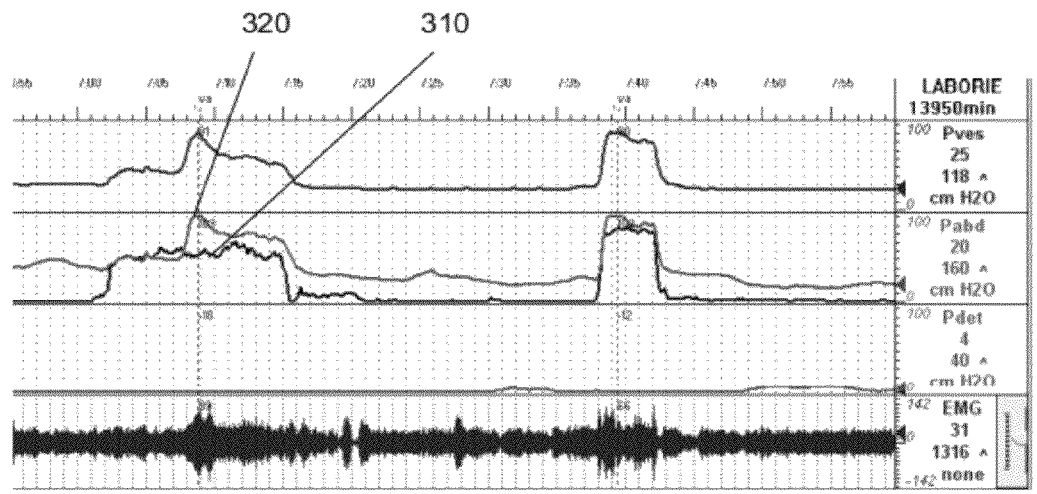

FIG. 2 illustrates a schematic diagram of the leak point pressure measuring device according to an embodiment of the present invention. The leak point pressure measuring device 203, as illustrated in FIG. 2, includes display 204, audible speaker 205, leak free fitting or connector 206, pressure chamber 208, pressure transducer or sensor 210, controller (or processor) 212, power source or battery 214, memory 216, transmission or communication module 218, and input source or button 220. Expelled air enters the device 203 through leak free fitting 206. Upon passing through leak free fitting 206, the air enters pressure chamber 208. Transducer or sensor 210 is connected to pressure chamber 208 and transmits a pressure signal to controller 212.

Controller 212 may include, for example, an integrated circuit that outputs a pressure reading to display 204. Power source or battery 214 is connected to controller 212 to provide a source of power to the circuit. Controller 212 may also send signals to speaker 205 in order to provide audible alerts. In at least one embodiment, controller 212 includes a programmed processor or electrical circuitry to detect the highest measured pressure since at least one of the start of a procedure or a Valsalva maneuver. The start of a procedure can be based on, for example, powering on the pressure measuring device or receiving a signal generate by a user interface such as a touch screen or button present on the device. The detection of a Valsalva maneuver in at least one embodiment is based on detecting a rise in the measured pressure reading from a based pressure reading. In at least one embodiment, when the high measured pressure is based on a Valsalva maneuver, the embodiment further including detection of when the measured pressures return to a level proximate to the base measured pressure as determined based on the measured pressure at the start of a procedure and after placement of the mouthpiece in the patient's mouth. The button may be additional button to button 220 or button 220 may be used for multiple purposes as discussed below.

Memory 216 is connected to controller 212 and may be utilized to store various data, e.g., pressure readings, alert levels, etc. The data file may take a variety of forms with the device storing pressure readings continuously, at predetermined intervals, or during detection of a Valsalva maneuver.

Communication module 218 may, for example, include a transmitter, a receiver, or a transceiver with any of these being wired or wireless. Communication module 218 is connected to controller 212 to enable the transmission (and in at least one embodiment the receipt) of data.

Input source or button 220 is connected to controller 212 to provide an input means. Input source 220 may be used, for example, to select various user functions or to mark data such as pressure readings. When a signal (or input) is received from button 220 during operation of the pressure measuring device, controller 212 will perform at least one of the following depending upon the implementation used for button 220: initiation of a procedure for tracking the highest measured pressure, annotating in memory with a flag or other leak indicator the most recent high measured pressure as causing a leak, annotating in memory with a flag or other leak indicator the most recent measured pressure as causing a leak, and ending data collection in response to button 220 being held done or pressed multiple times.

FIGS. 3A-3D illustrate graphs showing the experimental measurements of the lung pressure (Plung) and abdominal pressure (Pabd) of patients during Valsalva maneuvers. The graphs provide measurements of abdominal pressure (Pabd), intravesical pressure (Pves), and vesical delta pressure (Pdet) along the Y-axis over time along the X-axis. The abdominal pressure (Pabd) represents the pressure generated in the abdomen during Valsalva maneuvers. The intravesical pressure (Pves) is similar to the abdominal pressure (Pabd) but represents the pressure generated in the vesical or urinary bladder during Valsalva maneuvers. The vesical delta pressure (Pdet) represents the difference between the initial vesical pressure (with an empty bladder) and the vesical pressure during a Valsalva maneuvers.

FIG. 3A-3D illustrate the measured lung pressure (Plung) and abdominal pressure (Pabd) over time. The measured lung pressures (Plung) 310 and abdominal pressures (Pabd) 320 include measurements made during Valsalva maneuvers. The pressure measurements made during Valsalva maneuvers are illustrated by the rises in the plotted curves, i.e., rises in measured pressures. Each of FIGS. 3A-3D clearly illustrate the correlation between measured lung pressure (Plung) 310 and abdominal pressure (Pabd) 320. These measurements, as represented in the graphs, confirm the correlation between measured lung pressure (Plung) 310 and abdominal pressure (Pabd) 320. This correlation allows the abdominal pressure surrounding the bladder of an individual to be established by measuring the individual's lung pressure.

The abdominal leak point pressure measuring system and method of the present invention provide a non-invasive, simple, convenient and clean means of testing for Leak Point Pressure (LPP) of the human bladder. The system and method of the present invention can be used as a screening procedure before performing more extensive urodynamic studies.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Although the present invention has been described in terms of particular preferred and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the preferred and alternative embodiments described above can be configured without departing from the scope and spirit of the invention. Therefore, it is to be understood that, within the scope of the appended claims, the invention may be practiced other than as specifically described herein.

VI. EXPERIMENTAL USE SUPPORTING THE INVENTION

The present invention has undergone experimental use to test the concept as illustrated by the following discussion providing a summary of experimental use.

The following definitions described below are used throughout this section.
  a. "Menezes measures" is the measure generated by a device built according to an exemplary embodiment of the present invention as outlined herein.
  b. "Abd Abs" or abdominal absolute pressure is the pressure generated with Valsalva measured from zero.
  c. "ABD delta" or abdominal delta pressure is the difference between the pressure generated from a Valsalva from the initial abdominal pressure. This measure is not zero.
  d. "VES O ABS" is the vesical absolute pressure. This measure is similar to the abdominal absolute pressure but for vesical pressure.
  e. "VES O Delta" is the vesical delta pressure. This measure is similar to the abdominal delta pressure but for vesical pressure.
  f. "CNI" means uninhibited bladder contraction (contrações não-inibidas).
  g. "CIS" means bladder capacity.
  h. "IUEG" means urinary stress incontinence (incontinência urinária de esforço).
  i. "ABD-O" is the initial abdominal pressure with the bladder empty.

a. Sample Testing and Results

The degree of correlation between two quantitative (numeric) variables (x and y) is expressed by the correlation coefficient (r) which measures the degree of linear relation between the two. The value of the correlation coefficient (r) does not depend on the units in which x and y are expressed. The relatively large value of the correlation coefficient (r) indicates a strong relationship. See, *Medical Uses of Statistics*, edited by John C. Bailar, III, and Frederick Mosteller. Boston: NEJM Books, 1992 (second edition). R Square, the coefficient of determination, is the squared value of the correlation coefficient. R Square shows the amount of the variation in one variable that is explained by the other.

Test groups 1 and 2 were tested at different times with two different device prototypes. Both device prototypes produced similar test measurement correlations. As illustrated by the table below, the tests revealed no difference between people who were submitted to exam 1 or to exam 2 related to body mass index (BMI), age and CIS.

|   | n | Min. | Max. | Median | Mean | Std. Dev | p-value |
|---|---|---|---|---|---|---|---|
| BMI (body mass index) | | | | | | | |
| Group 1 | 26 | 17.78 | 37.81 | 26.94 | 26.96 | 4.51 | 0.38 |
| Group 2 | 33 | 19.83 | 34.70 | 25.44 | 25.86 | 3.91 | |
| Total | 59 | 17.78 | 37.81 | 26.03 | 26.35 | 4.18 | |
| Age | | | | | | | |
| Group 1 | 42 | 24 | 89 | 62 | 61.2 | 15.4 | 0.54 |
| Group 2 | 42 | 13 | 86 | 64 | 59.0 | 15.2 | |
| Total | 84 | 13 | 89 | 62.5 | 60.1 | 15.2 | |
| CIS | | | | | | | |
| Group 1 | 41 | 50 | 600 | 400 | 379.8 | 130.7 | 0.48 |
| Group 2 | 42 | 50 | 800 | 375 | 365.9 | 151.3 | |
| Total | 83 | 50 | 800 | 400 | 372.8 | 140.8 | |

Std. Dev = standard deviation

Overall Comparison

Tables 1 and 2 below, respectively, detail the observed correlation and determination coefficient of Menezes measures and other measures. Values of r are similar among these two exams except for CIS when exam 1 was better.

Table 1 below details the correlation and determination coefficients of "Menezes" measures and other measures according to vesical volume of exam 1.

TABLE 1

|  | 0 ml (n = 41) | | | 150 ml (n = 39) | | | 300 ml (n = 35) | | | CIS (n = 25) | | |
| --- | --- | --- | --- | --- | --- | --- | --- | --- | --- | --- | --- | --- |
|  | R | R square | p-value | R | R square | p-value | R | R square | p-value | R | R square | p-value |
| Abd Abs | 0.911 | 0.830 | <0.001 | 0.856 | 0.733 | <0.001 | 0.896 | 0.804 | <0.001 | 0.875 | 0.766 | <0.001 |
| ABD delta | 0.905 | 0.819 | <0.001 | 0.743 | 0.552 | <0.001 | 0.879 | 0.772 | <0.001 | 0.853 | 0.728 | <0.001 |
| VES O ABS | 0.889 | 0.790 | <0.001 | 0.815 | 0.664 | <0.001 | 0.883 | 0.779 | <0.001 | 0.824 | 0.678 | <0.001 |
| VES O Delta | 0.891 | 0.795 | <0.001 | 0.805 | 0.648 | <0.001 | 0.875 | 0.765 | <0.001 | 0.817 | 0.668 | <0.001 |

Table 2 below details the correlation and determination coefficients of "Menezes" measures and other measures according to vesical volume of exam 2.

TABLE 2

|  | 0 ml (n = 42) | | | 150 ml (n = 41) | | | 300 ml (n = 30) | | | CIS (n = 20) | | |
| --- | --- | --- | --- | --- | --- | --- | --- | --- | --- | --- | --- | --- |
|  | R | R square | p-value | R | R square | p-value | R | R square | p-value | R | R square | p-value |
| Abd Abs | 0.896 | 0.803 | <0.001 | 0.765 | 0.586 | <0.001 | 0.851 | 0.724 | <0.001 | 0.788 | 0.621 | <0.001 |
| ABD delta | 0.893 | 0.797 | <0.001 | 0.766 | 0.576 | <0.001 | 0.879 | 0.772 | <0.001 | 0.790 | 0.625 | <0.001 |
| VES O ABS | 0.899 | 0.807 | <0.001 | 0.791 | 0.626 | <0.001 | 0.852 | 0.726 | <0.001 | 0.765 | 0.585 | <0.001 |
| VES O Delta | 0.889 | 0.790 | <0.001 | 0.779 | 0.607 | <0.001 | 0.870 | 0.757 | <0.001 | 0.727 | 0.529 | <0.001 |

Prolapse a. Exam 1

Most patients in the test experienced no prolapse. Tables 3-6 below detail the observed values of correlation and determination coefficients for exam 1. Tables 7-10 below outline the observed values of correlation and determination coefficients for exam 2. All correlation coefficients were higher than 0.80 for exam 1 while some correlation coefficients were less than this cut-point for exam 2.

Table 3 below details the correlation and determination coefficients of "Menezes" measures and other measures of exam 1 according to the presence of prolapse (initial).

TABLE 3

|  | Yes | | | | No | | | |
| --- | --- | --- | --- | --- | --- | --- | --- | --- |
|  | n | R | R square | p-value | n | R | R square | p-value |
| Abd Abs | 2 | 1.0 | 1.0 | ... | 39 | 0.913 | 0.833 | <0.001 |
| ABD delta | 2 | 1.0 | 1.0 |  | 39 | 0.903 | 0.815 | <0.001 |
| VES O ABS | 2 | 1.0 | 1.0 |  | 39 | 0.889 | 0.791 | <0.001 |
| VES O Delta | 2 | 1.0 | 1.0 |  | 39 | 0.889 | 0.791 | <0.001 |

Table 4 below details the correlation and determination coefficients of "Menezes" measures and other measures of exam 1 according to the presence of prolapse (150 ml).

TABLE 4

|  | Yes | | | | No | | | |
| --- | --- | --- | --- | --- | --- | --- | --- | --- |
|  | n | R | R square | p-value | n | R | R square | p-value |
| Abd Abs | 2 | 1.0 | 1.0 |  | 36 | 0.854 | 0.729 | <0.001 |
| ABD delta | 2 | 1.0 | 1.0 |  | 36 | 0.838 | 0.702 | <0.001 |
| VES O ABS | 2 | 1.0 | 1.0 |  | 36 | 0.816 | 0.665 | <0.001 |
| VES O Delta | 2 | 1.0 | 1.0 |  | 36 | 0.810 | 0.656 | <0.001 |

Table 5 below details the correlation and determination coefficients of "Menezes" measures and other measures of exam 1 according to the presence of prolapse (300 ml).

TABLE 5

|  | Yes | | | | No | | | |
| --- | --- | --- | --- | --- | --- | --- | --- | --- |
|  | n | R | R square | p-value | n | R | R square | p-value |
| Abd Abs | 2 | 1.0 | 1.0 |  | 32 | 0.897 | 0.804 | <0.001 |
| ABD delta | 2 | 1.0 | 1.0 |  | 32 | 0.875 | 0.765 | <0.001 |
| VES O ABS | 2 | 1.0 | 1.0 |  | 32 | 0.879 | 0.772 | <0.001 |
| VES O Delta | 2 | 1.0 | 1.0 |  | 32 | 0.876 | 0.768 | <0.001 |

Table 6 below details the correlation and determination coefficients of "Menezes" measures and other measures of exam 1 according to the presence of prolapse (CIS).

TABLE 6

| | Yes | | | | No | | |
|---|---|---|---|---|---|---|---|
| | n | R | R square | p-value | n | R | R square | p-value |
| Abd Abs | 1 | ... | ... | ... | 23 | 0.868 | 0.753 | <0.001 |
| ABD delta | 1 | ... | ... | ... | 23 | 0.845 | 0.714 | <0.001 |
| VES O ABS | 1 | ... | ... | ... | 23 | 0.824 | 0.678 | <0.001 |
| VES O Delta | 1 | ... | ... | ... | 23 | 0.820 | 0.673 | <0.001 | b. Exam 2

Table 7 below details the correlation and determination coefficients of "Menezes" measures and other measures of exam 2 according to the presence of prolapse (initial).

TABLE 7

| | Yes | | | | No | | | |
|---|---|---|---|---|---|---|---|---|
| | n | R | R square | p-value | n | R | R square | p-value |
| Abd Abs | 4 | 0.898 | 0.806 | 0.102 | 38 | 0.894 | 0.799 | <0.001 |
| ABD delta | 4 | 0.995 | 0.990 | 0.005 | 38 | 0.888 | 0.788 | <0.001 |
| VES O ABS | 4 | 0.698 | 0.488 | 0.302 | 38 | 0.901 | 0.813 | <0.001 |
| VES O Delta | 4 | 0.873 | 0.762 | 0.127 | 38 | 0.888 | 0.789 | <0.001 |

Table 8 below details the correlation and determination coefficients of "Menezes" measures and other measures of exam 2 according to the presence of prolapse (150 ml).

TABLE 8

| | Yes | | | | No | | | |
|---|---|---|---|---|---|---|---|---|
| | n | R | R square | p-value | n | R | R square | p-value |
| Abd Abs | 4 | 0.846 | 0.717 | 0.154 | 37 | 0.757 | 0.573 | <0.001 |
| ABD delta | 4 | 0.980 | 0.960 | 0.020 | 37 | 0.757 | 0.573 | <0.001 |
| VES O ABS | 4 | 0.288 | 0.083 | 0.712 | 37 | 0.789 | 0.623 | <0.001 |
| VES O Delta | 4 | 0.688 | 0.473 | 0.312 | 37 | 0.773 | 0.598 | <0.001 |

Table 9 below details the correlation and determination coefficients of "Menezes" measures and other measures of exam 2 according to the presence of prolapse (300 ml).

TABLE 9

| | Yes | | | | No | | | |
|---|---|---|---|---|---|---|---|---|
| | n | R | R square | p-value | N | R | R square | p-value |
| Abd Abs | 3 | 0.617 | 0.381 | 0.576 | 27 | 0.846 | 0.716 | <0.001 |
| ABD delta | 3 | 0.202 | 0.041 | 0.871 | 27 | 0.873 | 0.762 | <0.001 |
| VES O ABS | 3 | 0.147 | 0.022 | 0.906 | 27 | 0.852 | 0.726 | <0.001 |
| VES O Delta | 3 | 0.772 | 0.595 | 0.439 | 27 | 0.863 | 0.745 | <0.001 |

Table 10 below details the correlation and determination coefficients of "Menezes" measures and other measures of exam 2 according to the presence of prolapse (CIS).

TABLE 10

| | Yes | | | | No | | | |
|---|---|---|---|---|---|---|---|---|
| | n | R | R square | p-value | n | R | R square | p-value |
| Abd Abs | 2 | 1.0 | 1.0 | ... | 18 | 0.821 | 0.674 | <0.001 |
| ABD delta | 2 | 1.0 | 1.0 | ... | 18 | 0.811 | 0.657 | <0.001 |
| VES O ABS | 2 | 1.0 | 1.0 | ... | 18 | 0.781 | 0.610 | <0.001 |
| VES O Delta | 2 | 1.0 | 1.0 | ... | 18 | 0.738 | 0.545 | <0.001 |

CNI (Involuntary Bladder Contractions)

Roughly half of patients (54.8%) in the test were presented with CNI. Among these patients, correlation coefficient was lower than 0.80 when considered volume of 300 ml and CSI (Tables 11-14). Exam 2 had different results. Correlation coefficients were lower than 0.80 among patients without CNI when considered volume of 150 ml. 300 ml and CIS (Tables 15-18).

a. Exam 1

Table 11 below details the correlation and determination coefficients of "Menezes" of exam 1 measures and other measures according to the presence of CNI (uninhibited bladder contraction) (initial).

TABLE 11

| | Yes | | | | No | | | |
|---|---|---|---|---|---|---|---|---|
| | N | R | R square | p-value | n | R | R square | p-value |
| Abd Abs | 17 | 0.951 | 0.905 | <0.001 | 23 | 0.871 | 0.759 | <0.001 |
| ABD delta | 17 | 0.947 | 0.896 | <0.001 | 23 | 0.863 | 0.744 | <0.001 |
| VES O ABS | 17 | 0.932 | 0.869 | <0.001 | 23 | 0.864 | 0.747 | <0.001 |
| VES O Delta | 17 | 0.934 | 0.873 | <0.001 | 23 | 0.879 | 0.773 | <0.001 |

Table 12 below details the correlation and determination coefficients of "Menezes" of exam 1 measures and other measures according to the presence of CNI (uninhibited bladder contraction) (150 ml).

TABLE 12

| | Yes | | | | No | | | |
|---|---|---|---|---|---|---|---|---|
| | n | R | R square | p-value | N | R | R square | p-value |
| Abd Abs | 15 | 0.861 | 0.742 | <0.001 | 23 | 0.861 | 0.741 | <0.001 |
| ABD delta | 15 | 0.826 | 0.683 | <0.001 | 23 | 0.878 | 0.771 | <0.001 |
| VES O ABS | 15 | 0.820 | 0.673 | <0.001 | 23 | 0.839 | 0.703 | <0.001 |
| VES O Delta | 15 | 0.824 | 0.679 | <0.001 | 23 | 0.828 | 0.685 | <0.001 |

Table 13 below details the correlation and determination coefficients of "Menezes" of exam 1 measures and other measures according to the presence of CNI (uninhibited bladder contraction) (300 ml).

TABLE 13

| | Yes | | | | No | | | |
|---|---|---|---|---|---|---|---|---|
| | n | R | R square | p-value | N | R | R square | p-value |
| Abd Abs | 11 | 0.783 | 0.613 | 0.004 | 23 | 0.933 | 0.870 | <0.001 |
| ABD delta | 11 | 0.698 | 0.487 | 0.017 | 23 | 0.935 | 0.875 | <0.001 |

TABLE 13-continued

|  | Yes | | | | No | | | |
|---|---|---|---|---|---|---|---|---|
|  | n | R | R square | p-value | N | R | R square | p-value |
| VES O ABS | 11 | 0.752 | 0.656 | 0.008 | 23 | 0.926 | 0.857 | <0.001 |
| VES O Delta | 11 | 0.751 | 0.564 | 0.008 | 23 | 0.922 | 0.850 | <0.001 |

Table 14 below details the correlation and determination coefficients of "Menezes" of exam 1 measures and other measures according to the presence of CNI (uninhibited bladder contraction) (CNI).

TABLE 14

|  | Yes | | | | No | | | |
|---|---|---|---|---|---|---|---|---|
|  | n | R | R square | p-value | N | R | R square | p-value |
| Abd Abs | 4 | 0.699 | 0.489 | 0.301 | 20 | 0.877 | 0.770 | <0.001 |
| ABD delta | 4 | 0.295 | 0.087 | 0.705 | 20 | 0.867 | 0.752 | <0.001 |
| VES O ABS | 4 | 0.437 | 0.191 | 0.563 | 20 | 0.837 | 0.701 | <0.001 |
| VES O Delta | 4 | 0.337 | 0.113 | 0.663 | 20 | 0.837 | 0.700 | <0.001 | b. Exam 2

Table 15 details the correlation and determination coefficients of "Menezes" of exam 2 measures and other measures according to the presence of CNI (uninhibited bladder contraction) (initial).

TABLE 15

|  | Yes | | | | No | | | |
|---|---|---|---|---|---|---|---|---|
|  | n | R | R square | p-value | n | R | R square | p-value |
| Abd Abs | 20 | 0.938 | 0.880 | <0.001 | 22 | 0.862 | 0.742 | <0.001 |
| ABD delta | 20 | 0.938 | 0.880 | <0.001 | 22 | 0.867 | 0.751 | <0.001 |
| VES O ABS | 20 | 0.938 | 0.881 | <0.001 | 22 | 0.876 | 0.768 | <0.001 |
| VES O Delta | 20 | 0.945 | 0.892 | <0.001 | 22 | 0.866 | 0.750 | <0.001 |

Table 16 below details the correlation and determination coefficients of "Menezes" of exam 2 measures and other measures according to the presence of CNI (uninhibited bladder contraction) (150 ml).

TABLE 16

|  | Yes | | | | No | | | |
|---|---|---|---|---|---|---|---|---|
|  | n | R | R square | p-value | N | R | R square | p-value |
| Abd Abs | 19 | 0.843 | 0.711 | <0.001 | 22 | 0.672 | 0.452 | 0.001 |
| ABD delta | 19 | 0.839 | 0.704 | <0.001 | 22 | 0.682 | 0.465 | <0.001 |
| VES O ABS | 19 | 0.900 | 0.811 | <0.001 | 22 | 0.688 | 0.474 | <0.001 |
| VES O Delta | 19 | 0.899 | 0.808 | <0.001 | 22 | 0.670 | 0.449 | 0.001 |

Table 17 below details the correlation and determination coefficients of "Menezes" of exam 2 measures and other measures according to the presence of CNI (uninhibited bladder contraction) (300 ml).

TABLE 17

|  | Yes | | | | No | | | |
|---|---|---|---|---|---|---|---|---|
|  | N | R | R square | p-value | N | R | R square | p-value |
| Abd Abs | 10 | 0.951 | 0.905 | <0.001 | 20 | 0.731 | 0.534 | <0.001 |
| ABD delta | 10 | 0.969 | 0.939 | <0.001 | 20 | 0.763 | 0.582 | <0.001 |
| VES O ABS | 10 | 0.968 | 0.937 | <0.001 | 20 | 0.746 | 0.557 | <0.001 |
| VES O Delta | 10 | 0.979 | 0.959 | <0.001 | 20 | 0.755 | 0.571 | <0.001 |

Table 18 below details the correlation and determination coefficients of "Menezes" of exam 2 measures and other measures according to the presence of CNI (uninhibited bladder contraction) (CIS).

TABLE 18

|  | Yes | | | | No | | | |
|---|---|---|---|---|---|---|---|---|
|  | N | R | R square | p-value | N | R | R square | p-value |
| Abd Abs | 6 | 0.984 | 0.968 | <0.001 | 14 | 0.599 | 0.359 | 0.024 |
| ABD delta | 6 | 0.978 | 0.956 | 0.001 | 14 | 0.614 | 0.377 | 0.020 |
| VES O ABS | 6 | 0.973 | 0.947 | 0.001 | 14 | 0.577 | 0.333 | 0.031 |
| VES O Delta | 6 | 0.965 | 0.931 | 0.002 | 14 | 0.565 | 0.319 | 0.035 |

VII. IUEG

Urinary Stress Incontinence

More than half of patients presented with IUEG in group 1 and group 2. Exam 1 had correlation coefficient higher than 0.80 when considered all volumes. Exam 2 had correlation coefficient lower than 0.80 when considered 150 ml (patients with IUEG) or considered CIS (patients without CIS).

a. Exam 1

Table 19 below details the correlation and determination coefficients of "Menezes" of exam 1 measures and other measures according to presence of IUEG (urinary stress incontinence) (initial).

TABLE 19

|  | Yes | | | | No | | | |
|---|---|---|---|---|---|---|---|---|
|  | n | R | R square | p-value | n | R | R square | p-value |
| Abd Abs | 13 | 0.855 | 0.732 | <0.001 | 27 | 0.929 | 0.864 | <0.001 |
| ABD delta | 13 | 0.805 | 0.648 | 0.001 | 27 | 0.932 | 0.868 | <0.001 |
| VES O ABS | 13 | 0.837 | 0.700 | <0.001 | 27 | 0.914 | 0.835 | <0.001 |
| VES O Delta | 13 | 0.814 | 0.663 | 0.001 | 27 | 0.917 | 0.840 | <0.001 |

Table 20 below details the correlation and determination coefficients of "Menezes" of exam 1 measures and other measures according to the presence of IUEG (urinary stress incontinence) (150 ml).

TABLE 20

|  | Yes | | | | No | | | |
| --- | --- | --- | --- | --- | --- | --- | --- | --- |
|  | n | R | R square | p-value | N | R | R square | p-value |
| Abd Abs | 13 | 0.889 | 0.790 | <0.001 | 25 | 0.839 | 0.704 | <0.001 |
| ABD delta | 13 | 0.867 | 0.752 | <0.001 | 25 | 0.834 | 0.695 | <0.001 |
| VES O ABS | 13 | 0.869 | 0.754 | <0.001 | 25 | 0.796 | 0.633 | <0.001 |
| VES O Delta | 13 | 0.844 | 0.712 | <0.001 | 25 | 0.802 | 0.643 | <0.001 |

Table 21 below details the correlation and determination coefficients of "Menezes" of exam 1 measures and other measures according to the presence of IUEG (urinary stress incontinence) (300 ml).

TABLE 21

|  | Yes | | | | No | | | |
| --- | --- | --- | --- | --- | --- | --- | --- | --- |
|  | n | R | R square | p-value | N | R | R square | p-value |
| Abd Abs | 13 | 0.928 | 0.861 | <0.001 | 21 | 0.882 | 0.777 | <0.001 |
| ABD delta | 13 | 0.924 | 0.853 | <0.001 | 21 | 0.860 | 0.740 | <0.001 |
| VES O ABS | 13 | 0.946 | 0.895 | <0.001 | 21 | 0.851 | 0.723 | <0.001 |
| VES O Delta | 13 | 0.927 | 0.860 | <0.001 | 21 | 0.859 | 0.738 | <0.001 |

Table 22 below details the correlation and determination coefficients of "Menezes" of exam 1 measures and other measures according to the presence of IUEG (urinary stress incontinence) (CIS).

TABLE 22

|  | Yes | | | | No | | | |
| --- | --- | --- | --- | --- | --- | --- | --- | --- |
|  | n | R | R square | p-value | N | R | R square | p-value |
| Abd Abs | 12 | 0.854 | 0.729 | <0.001 | 12 | 0.918 | 0.842 | <0.001 |
| ABD delta | 12 | 0.855 | 0.731 | <0.001 | 12 | 0.895 | 0.800 | <0.001 |
| VES O ABS | 12 | 0.864 | 0.747 | <0.001 | 12 | 0.828 | 0.685 | 0.001 |
| VES O Delta | 12 | 0.871 | 0.758 | <0.001 | 12 | 0.823 | 0.677 | 0.001 | b. Exam 2

Table 23 below details the correlation and determination coefficients of "Menezes" of exam 2 measures and other measures according to the presence of IUEG (urinary stress incontinence) (initial).

TABLE 23

|  | Yes | | | | No | | | |
| --- | --- | --- | --- | --- | --- | --- | --- | --- |
|  | n | R | R square | p-value | N | R | R square | p-value |
| Abd Abs | 18 | 0.886 | 0.785 | <0.001 | 24 | 0.908 | 0.824 | <0.001 |
| ABD delta | 18 | 0.873 | 0.763 | <0.001 | 24 | 0.919 | 0.845 | <0.001 |
| VES O ABS | 18 | 0.871 | 0.759 | <0.001 | 24 | 0.925 | 0.856 | <0.001 |
| VES O Delta | 18 | 0.860 | 0.740 | <0.001 | 24 | 0.922 | 0.850 | <0.001 |

Table 24 below details the correlation and determination coefficients of "Menezes" of exam 2 measures and other measures according to the presence of IUEG (urinary stress incontinence) (150 ml).

TABLE 24

|  | Yes | | | | No | | | |
| --- | --- | --- | --- | --- | --- | --- | --- | --- |
|  | n | R | R square | p-value | N | R | R square | p-value |
| Abd Abs | 18 | 0.685 | 0.470 | 0.002 | 23 | 0.810 | 0.656 | <0.001 |
| ABD delta | 18 | 0.675 | 0.455 | 0.002 | 23 | 0.816 | 0.666 | <0.001 |
| VES O ABS | 18 | 0.730 | 0.532 | 0.001 | 23 | 0.827 | 0.685 | <0.001 |
| VES O Delta | 18 | 0.719 | 0.516 | 0.001 | 23 | 0.812 | 0.660 | <0.001 |

Table 25 below details the correlation and determination coefficients of "Menezes" of exam 2 measures and other measures according to the presence of IUEG (urinary stress incontinence) (300 ml).

TABLE 25

|  | Yes | | | | No | | | |
| --- | --- | --- | --- | --- | --- | --- | --- | --- |
|  | n | R | R square | p-value | n | R | R square | p-value |
| Abd Abs | 13 | 0.958 | 0.918 | <0.001 | 17 | 0.800 | 0.640 | <0.001 |
| ABD delta | 13 | 0.977 | 0.955 | <0.001 | 17 | 0.836 | 0.698 | <0.001 |
| VES O ABS | 13 | 0.928 | 0.862 | <0.001 | 17 | 0.808 | 0.652 | <0.001 |
| VES O Delta | 13 | 0.972 | 0.944 | <0.001 | 17 | 0.818 | 0.668 | <0.001 |

Table 26 below details the correlation and determination coefficients of "Menezes" of exam 2 measures and other measures according to the presence of IUEG (urinary stress incontinence) (CIS).

TABLE 26

|  | Yes | | | | No | | | |
| --- | --- | --- | --- | --- | --- | --- | --- | --- |
|  | n | R | R square | p-value | N | R | R square | p-value |
| Abd Abs | 8 | 0.935 | 0.874 | 0.001 | 12 | 0.753 | 0.568 | 0.005 |
| ABD delta | 8 | 0.949 | 0.900 | <0.001 | 12 | 0.748 | 0.559 | 0.005 |
| VES O ABS | 8 | 0.921 | 0.849 | 0.001 | 12 | 0.704 | 0.496 | 0.011 |
| VES O Delta | 8 | 0.929 | 0.863 | 0.001 | 12 | 0.659 | 0.434 | 0.020 |

VIII. INFLUENCE OF CIS

A logistic regression of Menezes measure and ABD-O was performed also considering CIS in the model. There is no relation or influence of CIS in group 1 (p=0.636) or group 2 (0.726).

The invention claimed is:

1. A method for measuring an abdominal leak point pressure with a device having a pressure monitor and tubing connecting a mouthpiece to said pressure monitor, comprising:

placing the mouthpiece in the mouth of a patient;
    having the patient perform Valsalva maneuvers such that air is expelled from the lungs and forced through the tubing;
    measuring a pressure of the air expelled by the patient performing the Valsalva maneuvers with the pressure monitor;
    receiving a signal in response to detection of a urinary leak by the patient; and
    detecting at least one high measured pressure temporally associated with the signal; and determining an approximation of the abdominal Leak Point Pressure of the patient based on a correlation between the abdominal pressure and the at least one high measured pressure.

2. The method according to claim 1, wherein the measured pressure is used to represent the abdominal Leak Point Pressure of said patient.

3. The method according to claim 1, further comprising displaying a visual indication of the measured pressure with a digital display.

4. The method according to claim 1, further comprising providing an audible indication of the measured pressure with a speaker.

5. The method according to claim 1, wherein the mouthpiece includes a lip flange and bite wings in order to form a seal in the mouth of the patient.

6. The method according to claim 1, further comprising storing at least one measured pressure in a memory in communication with said pressure monitor.

7. The method according to claim 6, further comprising receiving a signal to annotate at least one temporaneously measured pressure reading.

8. The method according to claim 1, further comprising:
detecting a peak pressure in the plurality of measured pressures;
displaying the detected peak pressure on a display; and
storing the detected peak pressure in memory.

9. A method for measuring an abdominal leak point pressure with a device having a pressure monitor including a sensor and tubing connecting a mouthpiece to said pressure monitor, comprising:
placing the mouthpiece in the mouth of a patient, wherein the mouthpiece includes a lip flange and bite wings in order to form a seal in the mouth;
having the patient perform a Valsalva maneuver such that air is expelled from the lungs and forced through the tubing;
measuring a pressure of the expelled air with the pressure monitor;
receiving a signal to mark the pressure reading for an event;
storing the measured pressure in a memory and annotating the measured pressure data when the signal to mark is received; and
providing the measured pressure as representative of abdominal pressure.

10. The method according to claim 9, further comprising displaying a visual indication of the measured pressure with a digital display.

11. The method according to claim 9, further comprising providing an audible indication of the measured pressure with a speaker.

12. The method according to claim 9, further comprising transmitting the pressure reading to a remote device.

13. The method according to claim 9, further comprising:
detecting a peak pressure in the plurality of measured pressures;
displaying the detected peak pressure on a display; and
storing the detected peak pressure in memory.

14. A method of operation of a device that produces a series of pressure readings reflective of changes in abdominal pressure of a bladder to determine an abdominal leak point pressure where the device includes a non-invasive pressure monitor disposed outside a patient and connected to a mouthpiece directly or through tubing, the method comprising:
receiving an indication that the mouthpiece has been placed in the mouth of a patient;
measuring a pressure of air expelled by the patient performing a Valsalva maneuver such that air is expelled from the lungs and forced through the tubing and against a pressure sensor in the non-invasive pressure monitor;
displaying the measured pressure reading as representative of abdominal pressure;
receiving a signal to mark a measured pressure when the patient suffers a urinary leak;
detecting at least one high measured pressure;
when a mark signal is received, adding a leak indicator to a most recent high measured pressure;
storing the measured pressure in a memory;
transmitting to an external device at least one of any measured pressures that have an associated leak indicator, and
determining an approximation of the abdominal Leak Point Pressure of said patient based on a correlation between the abdominal pressure and the measured lung pressure.

15. The method according to claim 14, further comprising providing an audible indication of the measured pressure with a speaker.

16. The method according to claim 14, further comprising receiving at least one input signal for marking said pressure readings for a reason other than a urinary leak.

17. The method according to claim 14, further comprising converting said expelled air pressure into an abdominal pressure.

18. The method according to claim 14, wherein said detecting at least one high measured pressure includes determining when a Valsalva maneuver begins and detecting the highest measured pressure during that Valsalva maneuver.

19. The method according to claim 14, wherein said detecting at least one high measured pressure includes receiving a signal that a procedure has begun and determining if each measured pressure is the highest measured procedure during the procedure.

* * * * *